United States Patent [19]
Sredni et al.

[11] Patent Number: 5,654,328
[45] Date of Patent: Aug. 5, 1997

[54] METHOD AND COMPOSITION FOR REDUCING TUMOR DEVELOPMENT WITH A COMBINATION OF PLATINUM AND TELLURIUM OR SELENIUM COMPOUNDS

[76] Inventors: Benjamin Sredni, Shachal 3 Street, Kfar-Saba; Michael Albeck, 8 Harel Street-52444, Ramat-Gan, both of Israel

[21] Appl. No.: 357,127

[22] Filed: Dec. 15, 1994

[51] Int. Cl.⁶ .......................... A61K 31/335; A61K 31/35
[52] U.S. Cl. .......................... 514/450; 514/451; 514/452; 514/461; 514/463; 424/650; 424/702
[58] Field of Search .................... 514/450, 451, 514/452, 461, 463, 425, 449; 424/702, 650

[56] References Cited

U.S. PATENT DOCUMENTS 4,761,490  8/1988  Albeck et al. .......................... 549/347

*Primary Examiner*—John W. Rollins
*Attorney, Agent, or Firm*—Hedman, Gibson & Costigan, P.C.

[57] ABSTRACT

There are provided compositions for, and a method of, treating malignancies which comprise effective amounts of a novel combined therapy comprising a platinum compound and a tellurium or selenium compound, e.g., ammonium trichloro (dioxoethylene-O,O-tellurate), and administering the respective compounds simultaneously or separately.

13 Claims, 2 Drawing Sheets

METHOD AND COMPOSITION FOR REDUCING TUMOR DEVELOPMENT WITH A COMBINATION OF PLATINUM AND TELLURIUM OR SELENIUM COMPOUNDS

BACKGROUND OF THE INVENTION

The present invention provides a novel combination therapy for application to the treatment of neoplastic diseases.

The therapy is based on the sequential or concurrent administration of a platinum compound and a tellurium and/or a selenium compound in combination to provide an improved chemotherapeutic regimen for the treatment of neoplastic diseases or the treatment of malignant neoplasms. It has been discovered that the combination of a platinum compound and a tellurium and/or a selenium compound significantly reduces the development of tumor volume over what would be predicted from administration to tumor-infected mammals of either a platinum compound alone, or the tellurium and/or selenium compound, alone.

It has also been suggested in the prior art to use tellurium compounds in combination with other chemotherapeutic agents for the treatment of such malignant neoplasms. In fact, it is known that a combination of ammonium trichloro (dioxoethylene-O,O-tellurate) (AS101) and the known chemotherapeutic agent cyclophosphamide (CYP) shows synergism in extending the rate of survival of mice infected with Madison lung carcinoma tumor cells. Cancer Res. 51 (5)1499–1503 (1991).

It has now been discovered, and is the subject of the present invention, that a novel combination of the platinum compound cisplatin and a tellurium and/or a selenium compound shows an unexpectedly strong synergistic effect on the reduction in tumor volume in mice infected with cells of the solid tumor P388 and in L1210 leukemia.

Such findings are unexpected because the use of either the platinum compound alone or the tellurium and/or selenium compound alone at the same respective dosages produce anti-tumor effects which are shorter lasting and incrementally much closer to the saline control.

The present invention is concerned with a novel treatment regimen which combines a platinum compound and a tellurium and/or selenium compound. It also contemplates a novel composition with anti-neoplastic activity comprising a combination of a platinum compound and a tellurium and/or selenium compound. Among the preferred features of the invention are regimens and novel therapeutic combinations wherein the ratios of the platinum compound and tellurium and/or selenium compound provide synergistic activity, especially in the reduction of solid tumor growth.

It is therefore an object of the invention to provide novel therapeutic regimens and compositions which are based on the sequential or concurrent administration of novel combination of a platinum compound and a tellurium and/or selenium compound to mammals afflicted with neoplasms.

It is also an object of this invention to provide a novel method for the treatment of neoplastic diseases which uses a particular dose of a novel combination of a platinum compound and a tellurium and/or selenium compound.

These and other objects of the invention will become apparent from a review of the specification.

Brief Description of the Drawings FIG. 1 shows in graphical form the effect of administration of the citrate buffer control, cisplatin, the tellurium compound, ammonium trichloro(dioxoethylene-O, O-tellurate) (AS101) and the combination of the cisplatin, the tellurium compound, ammonium trichloro(dioxoethylene-O,O-tellurate) (AS101) on the development of solid P388 tumor in vivo over a 32 day period in mice.

FIG. 2 shows in graphical form the effect of administration of the citrate buffer control, cisplatin, the tellurium compound, ammonium trichloro(dioxoethylene-O,O-tellurate) (AS101) and the combination of the cisplatin, the tellurium compound, ammonium trichloro(dioxoethylene-O,O-tellurate) (AS101) on the development of L1210 leukemia in vivo over a 32 day period in mice.

SUMMARY OF THE INVENTION

In accordance with the present invention there is provided a method of treating malignancies which are sensitive to the combination of a platinum compound, and a tellurium and/or selenium compound, said method comprising administering, sequentially or concurrently, an amount of the combination which is effective to treat malignancies which are sensitive to the combination.

Preferred features of the invention comprise administering the combination in weight ratios which are synergistically-effective to treat malignancies, especially solid tumors. Cisplatin is preferred but other platinum compounds, such as carboplatin and other platinum compounds, can be used. Ammonium trichloro (dioxoethylene-O,O-tellurate) (AS101) is preferred but other tellurium and/or selenium compounds, such as dichlorodioxoethylene-O,O-tellurate, and the corresponding selenium isosteres, may be employed.

DETAILED DESCRIPTION OF THE INVENTION

Figure 1:
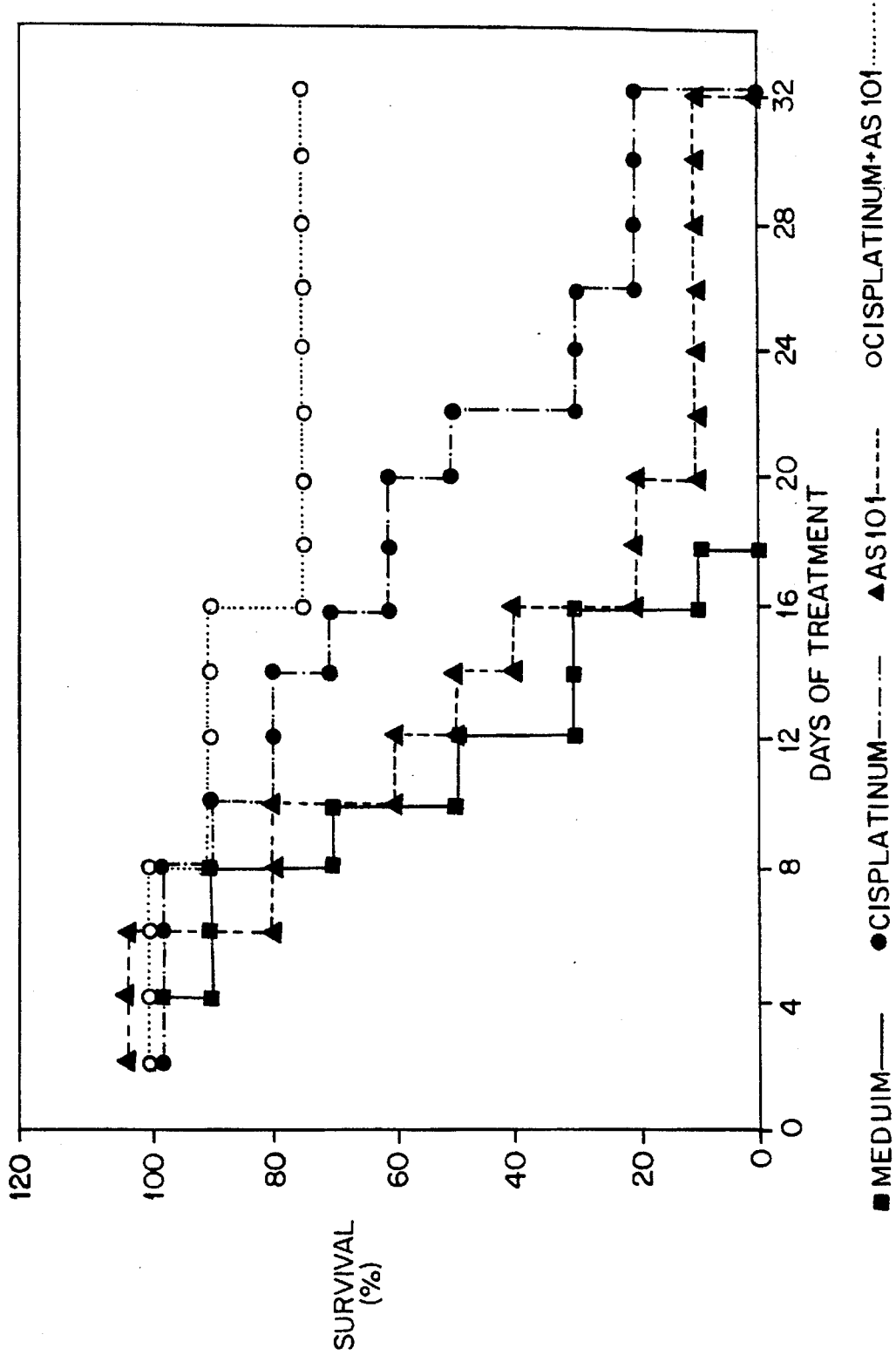
Figure 2:
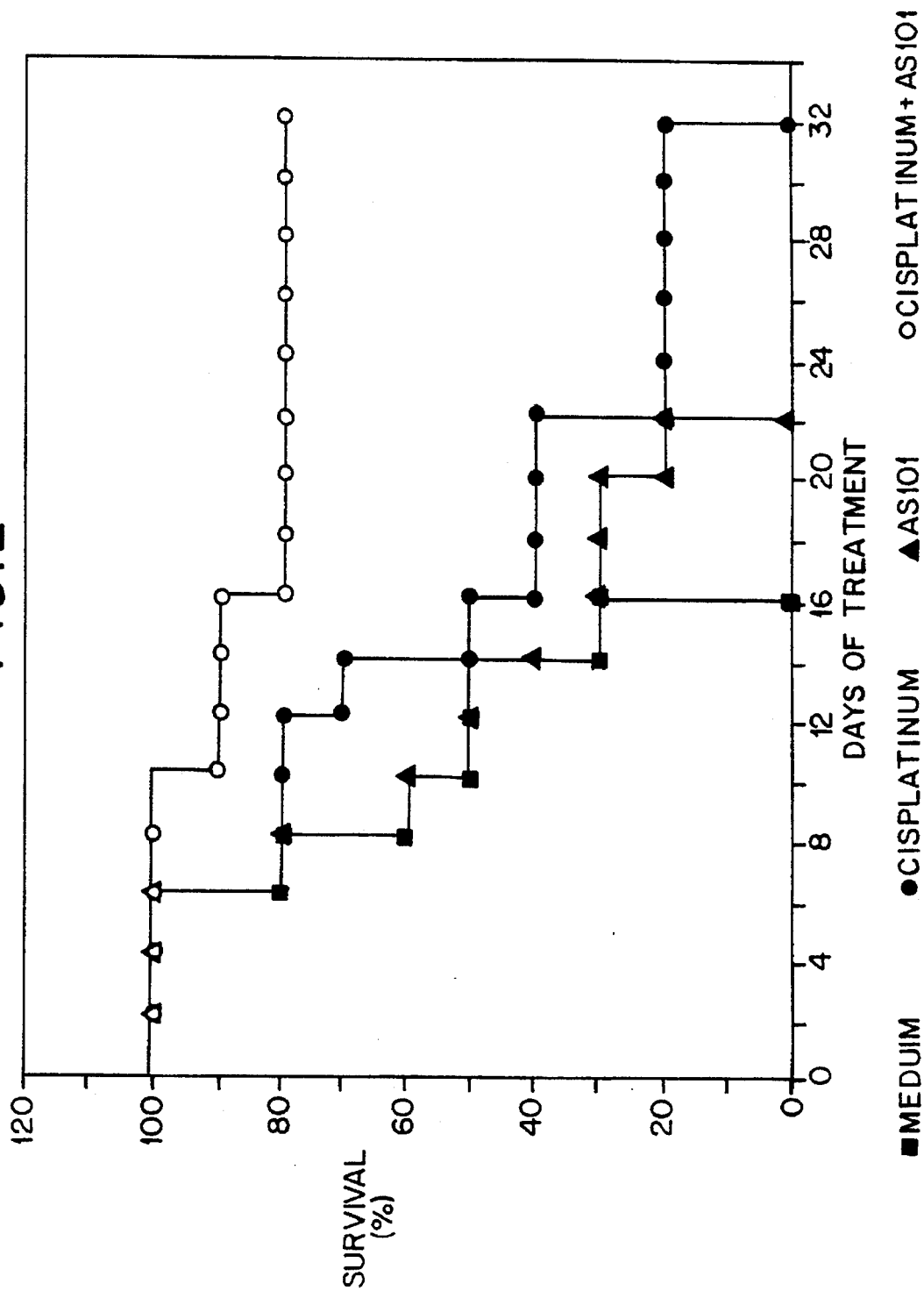

The tellurium compounds for use in the invention include those of the formula:

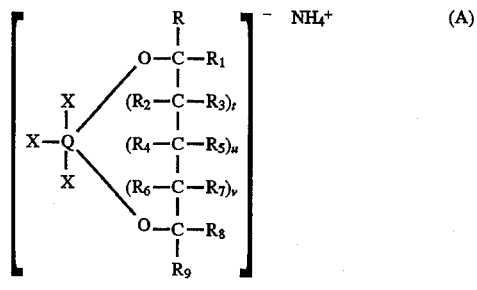 (A)

or

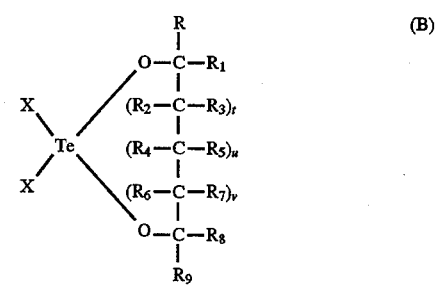 (B)

or

TeX$_4$ (C)

or

TeO$_2$ (D)

or

PhTeCl$_3$ (E)

or

-continued $$(C_6H_5)^+P(TeCl_3(O_2C_2H_4))^- \quad (F)$$

wherein Q is Te or Se; t is 1 or 0; u is 1 or 0; v is 1 or 0; R, $R_1$, $R_2$, $R_3$, $R_4$, $R_5$, $R_6$, $R_7$, $R_8$ and $R_9$ are the same or different and are independently selected from the group consisting of hydrogen, hydroxyalkyl of 1 to 6 carbons, hydroxy, alkyl of from 1 to 6 carbon atoms, halogen, haloalkyl of 1 to 6 carbon atoms, carboxy, alkylcarbonylalkyl of 2 to 10 carbons, alkanoyloxy of 1 to 6 carbon atoms, carboxyalkyl of 1 to 6 carbon atoms, acyl, amido, cyano, amidoalkyl of 1 to 6 carbons, N-monoalkylamidoalkyl of 2 to 10 carbons, N,N-dialkylamidoalkyl of 4 to 10 carbons, cyanoalkyl of 1 to 6 carbons, alkoxy of 1 to 6 carbon atoms, alkoxyalkyl of 2 to 10 carbon atoms and —$COR_{10}$ wherein $R_{10}$ is alkyl of from 1 to 6 carbons; and X is halogen. Although the ammonium salt is illustrated, it is understood that other pharmaceutically acceptable salts are within the scope of the invention. The compounds with the five membered rings are preferred.

As used herein, for compounds of formulae (A) and (B), the term alkyl of 1 to 6 carbon atoms includes straight and branched chain alkyl groups such as methyl; ethyl; n-propyl; n-butyl, and the like; the term hydroxyalkyl of 1 to 6 carbon atoms includes hydroxymethyl; hydroxyethyl; hydroxy-n-butyl; the term haloalkyl of 1 to 6 carbon atoms includes chloromethyl; 2-iodoethyl; 4-bromo-n-butyle; iodoethyl; 4-bromo-n-pentyl and the like; the term alkanoyloxy of 1 to 6 carbon atoms includes acetyl, propionyl, butanoyl and the like; the term carboxyalkyl includes carboxymethyl, carboxyethyl, ethylenecarboxy and the like; the term alkylcarbonylalkyl includes methanoylmethyl, ethanoylethyl and the like; the term amidoalkyl includes —$CH_2CONH_2$; —$CH_2CH_2CONH_2$; —$CH_2CH_2CH_2CONH_2$ and the like; the term cyanoalkyl includes —$CH_2CN$; —$CH_2CH_2CN$; —$CH_2CH_2CH_2CN$ and the like; the term alkoxy of 1 to 6 carbon atoms includes methoxy, ethoxy, n-propoxy, n-pentoxy and the like; the terms halo and halogen are used to signify chloro, bromo, iodo and fluoro; the term acyl includes $R_{16}CO$ wherein $R_{16}$ is H, or alkyl of 1 to 6 carbons such as methanoyl, ethanoyl and the like; the term aryl includes phenyl, alkylphenyl and naphthyl; the term N-monoalkylamidoalkyl includes —$CH_2CH_2CONHCH_3$, —$CH_2CONHCH_2CH_3$; the term N,N-dialkylamidoalkyl includes —$CH_2CON(CH_3)_2$; $CH_2CH_2CON(CH_2CH_3)$. Compounds which are based on tellurium are the presently preferred compounds of the invention.

Ammonium (trichloro(dioxoethylene-O,O-tellurate) is a compound of the structure

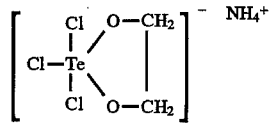

This compound is a member of a family of organic 9,10,11 derivatives of tellurium and selenium found to have the ability to stimulate the in vivo and in vitro production of cytokines and their receptors. As is set forth in U.S. Pat. No. 4,761,490, these compounds may be utilized in the treatment of certain tumors, autoimmune diseases, immune diseases and infectious diseases.

The derivatives of tellurium or selenium that are useful in the present invention include those compounds of the above mentioned general formulas (A)–(F) which stimulate cells to produce lymphokines.

The compounds are made by combining substantially equimolar amounts of the reactants in a suitable reactor at room temperature or at elevated temperatures up to the reflux temperature. It is preferred to utilize a solvent that is capable of dissolving the reactants such as acetonitrile, benzene, toluene, xylene, dimethylsulfoxide, mixtures thereof and the like. Compounds of structure (A) are only obtained in acetonitrile. The preferred method requires heating the reaction mixture to the reflux temperature of the solvent while stirring the reaction mixture with a suitable magnetic or mechanical stirrer. The reaction may be carried out for a sufficient period of time to ensure complete reaction of the reactants. This time will vary with the reaction conditions, the particular compound being made and the nature of the solvents. The reaction may be run at atmospheric pressure but if desired may be carried out at reduced or elevated pressure. The reaction is practically carried out in the presence of an oxygen containing atmosphere such as air but inert atmospheres such as nitrogen, argon, helium or mixtures thereof may be utilized if desired. Reaction times of 1 minute to 168 hours may be used although reaction times of 6–16 hours are preferred Other compounds which are based on tellurium and may be used in the practice of the invention include $PhTeCl_3$, $TeO_2$ and $TeX_4$ $(C_6H_5)_4$ P+ $(TeCl_3(O_2C_2H_4))$—(Z. Naturforsh, 36, 307–312 (1981). Compounds of the following structure are also included:

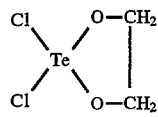

These compounds are described in U.S. Pat. No. 4,761, 490 which is incorporated by reference. In addition, $TeCl_4$; $TeBr_4$ and compounds which give in aqueous solution $TeO_2$ preferably in the form of a complex such as for example $TeO_2$ complex with citric acid or ethylene glycol.

The platinum compounds are described in the literature include those compounds described in U.S. Pat. Nos. 4,500, 465; 4,410,544; JP-255943; U.K. 2,024,823; U.K. 2,128, 615A; U.S. Pat. Nos. 4,730,069 and 4,140,707, all of which are incorporated by reference.

For the treatment of malignancies which are susceptible to treatment, the tellurium compound may be administered by the oral, intramuscular, intravenous, transdermal or intraperitoneal route to mammals including humans. The oral dose will be 0.15 to 0.5 mg/kg of body weight daily and preferably from 0.03 to 0.1 mg/kg of body weight daily in one dose or in divided doses. The parenteral dose will be 0.03 to 0.2 mg/kg of body weight daily and preferably from 0.006 to 0.02 mg/kg daily given as a bolus injection or as a continuous parenteral infusion. The dose of the platinum compound to be used is an effective amount to exert an anti-tumor effect on the particular tumor which is being treated. The dose will depend on the particular platinum compound and these doses are disclosed in the literature. In the case of cisplatin the dose will depend upon the condition which is treated and may be from 20 mg/m² daily for 5 days or 100 mg/m² once every 4 weeks. Carboplatin may be administered at a dose of 360 mg/m² once every 4 weeks. The PDR, 1994 Edition at pages 662–669 discloses how to use cisplatin and carboplatin and these pages are incorporated by reference.

Combined compositions of the platinum compound and the tellurium compound may comprise from about 90 to about 10 parts by weight of the platinum compound and from 10 to 90 parts by weight of the tellurium or selenium compound.

The invention may be used to treat benign tumor and malignancies which are sensitive to the described treatment regimen. The malignancies may be primary or metastatic such as solid tumors, leukemias or lymphomas. These malignancies include colorectal carcinoma, espohageal carcinoma, stomach carcinoma, pancreatic carcinoma, liver carcinoma, small bowel carcinoma, lung tumors, CML, mesothelioma, melanomas, biliary carcinoma, breast carcinoma and adenocarcinoma of unknown origin.

DESCRIPTION OF THE PREFERRED EMBODIMENTS

EXAMPLE 1

DBA/2J mice, 18–22 g. both male and female were used to confirm the activity of ammonium trichloro (O,O'-dioxoethylene tellurate) and cisplatin.

Each mouse received intraperitoneally, 0.5 ml of a $1 \times 10^6$ viable tumor cells of the P388 tumor cell line suspension in saline on day 1. Ammonium trichloro (O,O'-dioxoethylene tellurate) and cisplatin were dissolved in 0.05M citrate buffer, pH 6.4. The solution of ammonium trichloro (O,O'-dioxoethylene tellurate) contained 50 mg/ml and the solution of cisplatin contained 750 mg/ml. The solutions were freshly prepared or kept at 4° C. for a maximum period of 48 hours prior to use. Drugs were administered peritoneally with an initial treatment 24 hours after tumor inoculation. In the treatment of the mice with the P388 tumor, the treatment schedules were as follows: (a) cisplatin: one injection of 150 mg/mouse days 1, 4 and 7; (b) ammonium trichloro (O,O'-dioxoethylene tellurate): one injection of 10 mg/mouse every second day until end of treatment. Four groups of mice with 10 mice in each group were treated as follows: (1) citrate buffer as control; (2) cisplatin alone; (3) ammonium trichloro (O,O'-dioxoethylene tellurate) alone and (4) a combined therapy of cisplatin alone and ammonium trichloro (O,O'-dioxoethylene tellurate).

The synergistic antitumor effect of ammonium trichloro (O,O'-dioxoethylene tellurate) and cisplatin in the P-388 leukemia tumor bearing mice significantly enhanced survival of treated mice. As shown in FIG. 1, combined treatment of ammonium trichloro (O,O'-dioxoethylene tellurate) and paclitaxel resulted in 75% survival of all treated animals by day 32 ($p<0.01$). Cisplatin alone enhanced the rate of survival for a limited period of time with no survivors on day 32 after tumor implantation. Ammonium trichloro (O,O'-dioxoethylene tellurate) alone was very similar to the control, showing no significant cumulative effect on the percentage of survival.

The cumulative percentage of survival of mice treated with ammonium trichloro (O,O'-dioxoethylene tellurate) and cisplatin was significantly higher compared to control mice ($p<0.05$). When cisplatin was administered alone, it had a slight but non-significant effect on the cumulative percentage survival of mice.

A second series of experiments was carried out with the L-1210 tumor cell line with same type of mice that were used in the experiments described above. The mice were inoculated with $1 \times 10^6$ viable L-1210 tumor cells according to the dosage schedule and the treatment regimen set forth above.

The test data showed that the L-1210 tumor cell line is less sensitive to cisplatin alone which showed a limited and non-significant effect on the rate of survival by day 32. Ammonium trichloro (O,O'-dioxoethylene tellurate) alone had a very slight effect with no survivors after 22 days. Both ammonium trichloro (O,O'-dioxoethylene tellurate) and cisplatin alone did not have any significant effect on the cumulative percentage of survival.

In contrast, the combination of ammonium trichloro (O,O'-dioxoethylene tellurate) and cisplatin showed a clear synergistic effect resulting in 80% survival by day 32 ($p<0.01$) and a significant effect ($p<0.01$) on the cumulative percentage or survival compared to the control or ammonium trichloro (O,O'-dioxoethylene tellurate) or cisplatin alone.

We claim:

1. A composition comprising a combination of a platinum compound and a tellurium or selenium compound in respective amounts effective to treat malignancies so as to produce more than a merely additive increase in therapeutic effect when compared to the platinum compound and the tellurium or selenium compound used alone, said tellurium or selenium compound being selected from the group consisting of those of the formulae:

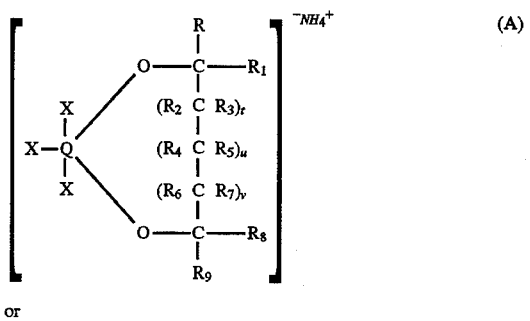

(A)

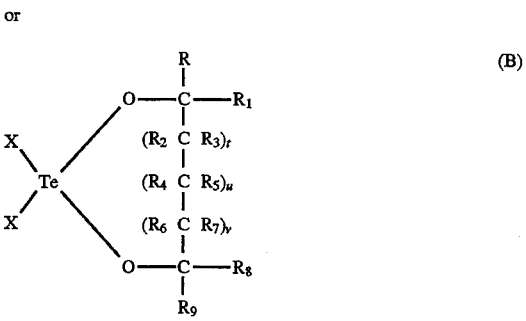

(B)

or

TeX$_4$      (C)

or

TeO$_2$      (D)

or

PhTeCl$_3$      (E)

or $(C_6H_5)^+P(TeCl_3(O_2C_2H_4))^-$      (F)

wherein Q is Te or Se; t is 1 or 0; u is 1 or 0; v is 1 or 0; R, $R_1$, $R_2$, $R_3$, $R_4$, $R_5$, $R_6$, $R_7$, $R_8$ and $R_9$ are the same or different and are independently selected from the group consisting of hydrogen, hydroxyalkyl of 1 to 6 carbons, hydroxy, alkyl of from 1 to 6 carbon atoms, halogen, haloalkyl of 1 to 6 carbon atoms, carboxy, alkylcarbonylalkyl of 2 to 10 carbons, alkanoyloxy of 1 to 6 carbon atoms, carboxyalkyl of 1 to 6 carbon atoms, acyl, amido, cyano, amidoalkyl of 1 to 6 carbons, N-monoalkylamidoalkyl of 2 to 10 carbons, N,N-dialkylamidoalkyl of 4 to 10 carbons, cyanoalkyl of 1 to 6 carbons, alkoxy of 1 to 6 carbon atoms, alkoxyalkyl of 2 to 10 carbon atoms and —COR$_{10}$ wherein R$_{10}$ is alkyl of from 1 to 6 carbons; and X is halogen.

2. A composition comprising a combination of from 10 to 90 parts by weight of a platinum compound and from 90 to 10 parts by weight of a tellurium compound in respective amounts effective to treat malignancies so as to produce more than a merely additive increase in therapeutic effect when compared to the platinum compound and the tellurium compound used alone, said tellurium compound being selected from the group consisting of those of the formulae:

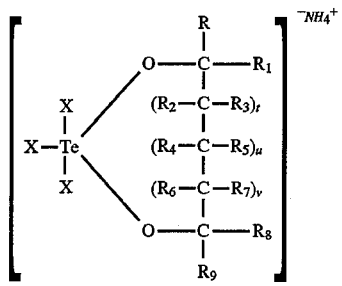

or

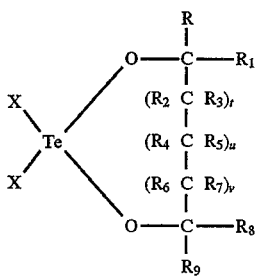

or
TeX$_4$ (C)
or
TeO$_2$ (D)
or
PhTeCl$_3$ (E)
or
(C$_6$H$_5$)$^+$P(TeCl$_3$(O$_2$C$_2$H$_4$))$^-$ (F)

wherein t is 1 or 0; u is 1 or 0; v is 1 or 0; R, R$_1$, R$_2$, R$_3$, R$_4$, R$_5$, R$_6$, R$_7$, R$_8$ and R$_9$ are the same or different and are independently selected from the group consisting of hydrogen, hydroxyalkyl of 1 to 6 carbons, hydroxy, alkyl of from 1 to 6 carbon atoms, halogen, haloalkyl of 1 to 6 carbon atoms, carboxy, alkylcarbonylalkyl of 2 to 10 carbons, alkanoyloxy of 1 to 6 carbon atoms, carboxyalkyl of 1 to 6 carbon atoms, acyl, amido, cyano, amidoalkyl of 1 to 6 carbons, N-monoalkylamidoalkyl of 2 to 10 carbons, N,N-dialkylamidoalkyl of 4 to 10 carbons, cyanoalkyl of 1 to 6 carbons, alkoxy of 1 to 6 carbon atoms, alkoxyalkyl of 2 to 10 carbon atoms and —COR$_{10}$ wherein R$_{10}$ is alkyl of from 1 to 6 carbons; X is halogen and complexes of said tellurium compound.

3. A composition as defined in claim 2 wherein the platinum compound is selected from the group consisting of cisplatin and carboplatin.

4. A composition as defined in claim 2 wherein the platinum compound is cisplatin.

5. A composition as defined in claim 2 wherein the platinum compound is carboplatin.

6. A composition as defined in claim 2 wherein the tellurium compound is ammonium trichloro(dioxoethylene-O,O-tellurate).

7. A method of treating a benign tumor or malignancies which are sensitive to the combined therapy of a taxane compound and a tellurium or selenium compound, said method comprising administering simultaneously or separately, an amount of each drug which is synergistically-effective to treat benign tumors or malignancies which are sensitive to the combined therapy, said tellurium or selenium compound being selected from the group consisting of those of the formulae:

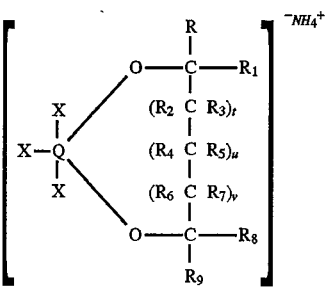

or

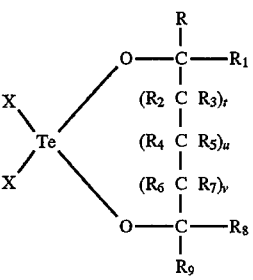

or
TeX$_4$ (C)
or
TeO$_2$ (D)
or
PhTeCl$_3$ (E)
or
(C$_6$H$_5$)$^+$P(TeCl$_3$(O$_2$C$_2$H$_4$))$^-$ (F)

wherein Q is Te or Se; t is 1 or 0; u is 1 or 0; v is 1 or 0; R, R$_1$, R$_2$, R$_3$, R$_4$, R$_5$, R$_6$, R$_7$, R$_8$ and R$_9$ are the same or different and are independently selected from the group consisting of hydrogen, hydroxyalkyl of 1 to 6 carbons, hydroxy, alkyl of from 1 to 6 carbon atoms, halogen, haloalkyl of 1 to 6 carbon atoms, carboxy, alkylcarbonylalkyl of 2 to 10 carbons, alkanoyloxy of 1 to 6 carbon atoms, carboxyalkyl of 1 to 6 carbon atoms, acyl, amido, cyano, amidoalkyl of 1 to 6 carbons, N-monoalkylamidoalkyl of 2 to 10 carbons, N,N-dialkylamidoalkyl of 4 to 10 carbons, cyanoalkyl of 1 to 6 carbons, alkoxy of 1 to 6 carbon atoms, alkoxyalkyl of 2 to 10 carbon atoms and —COR$_{10}$ wherein R$_{10}$ is alkyl of from 1 to 6 carbons; and X is halogen.

8. A method of treating a benign tumor or malignancies which are sensitive to the combined therapy of a platinum compound and a tellurium compound, said method comprising administering simultaneously or separately, an amount of each drug which is synergistically-effective, said synergistically effective amount being from 10 to 90 parts by weight of said platinum compound and from 90 to 10 parts by weight of a tellurium compound to treat benign tumors or malignancies which are sensitive to the combined therapy, said tellurium compound being selected from the group consisting of those of the formulae:

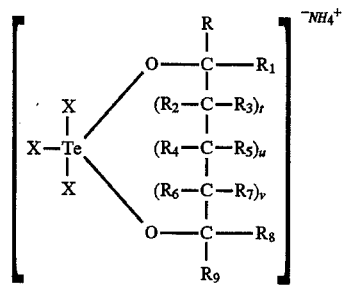

or

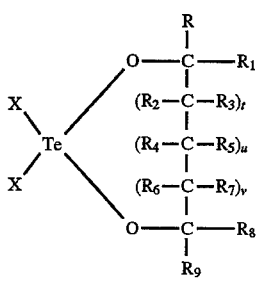

or
TeX₄ (C)
or
TeO₂ (D)
or
PhTeCl₃ (E)
or
$(C_6H_5)^+P(TeCl_3(O_2C_2H_4))^-$ (F)

wherein t is 1 or 0; u is 1 or 0; v is 1 or 0; R, $R_1$, $R_2$, $R_3$, $R_4$, $R_5$, $R_6$, $R_7$, $R_8$ and $R_9$ are the same or different and are independently selected from the group consisting of hydrogen, hydroxyalkyl of 1 to 6 carbons, hydroxy, alkyl of from 1 to 6 carbon atoms, halogen, haloalkyl of 1 to 6 carbon atoms, carboxy, alkylcarbonylalkyl of 2 to 10 carbons, alkanoyloxy of 1 to 6 carbon atoms, carboxyalkyl of 1 to 6 carbon atoms, acyl, amido, cyano, amidoalkyl of 1 to 6 carbons, N-monoalkylamidoalkyl of 2 to 10 carbons, N,N-dialkylamidoalkyl of 4 to 10 carbons, cyanoalkyl of 1 to 6 carbons, alkoxy of 1 to 6 carbon atoms, alkoxyalkyl of 2 to 10 carbon atoms and —$COR_{10}$ wherein $R_{10}$ is alkyl of from 1 to 6 carbons; and X is halogen.

9. A method as defined in claim 8 wherein the platinum compound is selected from cisplatin and carboplatin.

10. A method as defined in claim 8 wherein the tellurium compound is ammonium trichloro(dioxoethylene-O,O-tellurate), a compound of formula (A) wherein Q is tellurium; R, $R_1$, $R_8$ and $R_9$ are hydrogen; and t, u, and v are 0.

11. A method as defined in claim 8 wherein the platinum compound and the tellurium compound are administered sequentially.

12. A method as defined in claim 8 wherein the platinum compound and the tellurium compound are administered simultaneously.

13. A method of treating a benign tumor or malignancies which are sensitive to the combined therapy of a platinum compound and a tellurium compound, said method comprising administering simultaneously or separately, an amount of each drug which is synergistically-effective, said synergistically effective amount being from 10 to 90 parts by weight of said platinum compound and from 90 to 10 parts by weight of a tellurium compound, to a host in order to treat benign tumors or malignancies which are sensitive to the combined therapy, said tellurium compound being selected from the group consisting of those of the formulae:

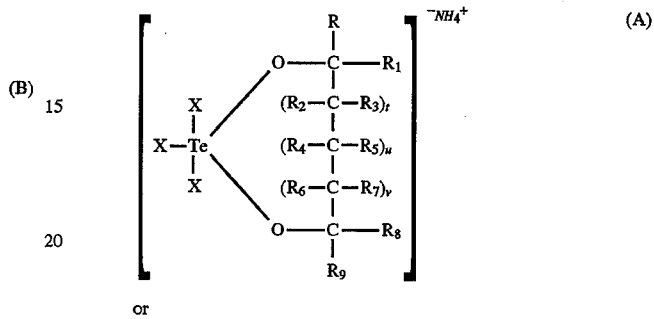

or

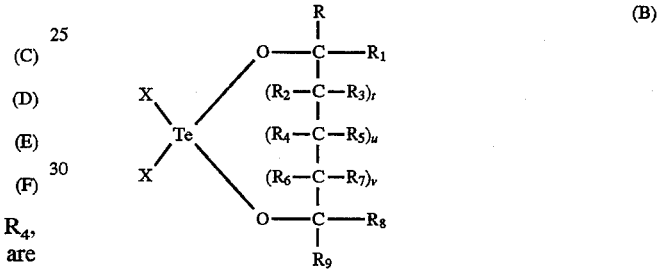

or
TeX₄ (C)
or
TeO₂ (D)
or
PhTeCl₃ (E)
or
$(C_6H_5)^+P(TeCl_3(O_2C_2H_4))^-$ (F)

wherein t is 1 or 0; u is 1 or 0; v is 1 or 0; R, $R_1$, $R_2$, $R_3$, $R_4$, $R_5$, $R_6$, $R_7$, $R_8$ and $R_9$ are the same or different and are independently selected from the group consisting of hydrogen, hydroxyalkyl of 1 to 6 carbons, hydroxy, alkyl of from 1 to 6 carbon atoms, halogen, haloalkyl of 1 to 6 carbon atoms, carboxy, alkylcarbonylalkyl of 2 to 10 carbons, alkanoyloxy of 1 to 6 carbon atoms, carboxyalkyl of 1 to 6 carbon atoms, acyl, amido, cyano, amidoalkyl of 1 to 6 carbons, N-monoalkylamidoalkyl of 2 to 10 carbons, N,N-dialkylamidoalkyl of 4 to 10 carbons, cyanoalkyl of 1 to 6 carbons, alkoxy of 1 to 6 carbon atoms, alkoxyalkyl of 2 to 10 carbon atoms and —$COR_{10}$ wherein $R_{10}$ is alkyl of from 1 to 6 carbons; X is halogen and complexes of said tellurium compound.

* * * * *